US007666307B2

(12) United States Patent
Van Den Mooter et al.

(10) Patent No.: US 7,666,307 B2
(45) **Date of Patent: *Feb. 23, 2010**

(54) PARTICLE SIZE REDUCTION OF BIOACTIVE COMPOUNDS

(75) Inventors: Guy Van Den Mooter, Pellenberg (BE); Johan Martens, Huldenberg (BE); Jan Nuyens, Antwerp (BE)

(73) Assignee: K.U. Leuven Research & Development, Leuven (BE)

( * ) Notice: Subject to any disclaimer, the term of this patent is extended or adjusted under 35 U.S.C. 154(b) by 384 days.

This patent is subject to a terminal disclaimer.

(21) Appl. No.: 10/595,119

(22) PCT Filed: Aug. 25, 2004

(86) PCT No.: PCT/BE2004/000121

§ 371 (c)(1),
(2), (4) Date: Feb. 23, 2006

(87) PCT Pub. No.: WO2005/018611

PCT Pub. Date: Mar. 3, 2005

(65) Prior Publication Data

US 2007/0082054 A1 Apr. 12, 2007

(30) Foreign Application Priority Data

Aug. 26, 2003 (GB) ................................ 0319797.7

(51) Int. Cl.
*B02C 19/00* (2006.01)

(52) U.S. Cl. ................................ 210/695; 241/1; 241/5

(58) Field of Classification Search ................. 210/695; 241/5

See application file for complete search history.

(56) References Cited

U.S. PATENT DOCUMENTS

| | | | |
|---|---|---|---|
| 3,133,023 | A | 5/1964 | Vogel et al. |
| 4,676,439 | A | 6/1987 | Saito et al. |
| 5,145,684 | A | 9/1992 | Liversidge et al. |
| 5,922,355 | A | 7/1999 | Parikh et al. |
| 6,203,768 | B1 | 3/2001 | McCormick et al. |
| 6,221,400 | B1 | 4/2001 | Liversidge et al. |

(Continued)

FOREIGN PATENT DOCUMENTS

| | | |
|---|---|---|
| AT | 410 171 | 2/2003 |

(Continued)

OTHER PUBLICATIONS

Cui and Hahn, "Tensile Deformation of Nanostructured $TiO_2$ at Low Tempatures," *Nanostructured Materials* 1: 419-425 (1992).

(Continued)

*Primary Examiner*—David A Reifsnyder
(74) *Attorney, Agent, or Firm*—Clark & Elbing LLP

(57) ABSTRACT

The invention provides a method for reducing the average size of biologically active compound particles or agglomerates suspended in a fluid by flowing one or more times said fluid having biologically active compound particles or agglomerates suspended therein through one or more magnetic fields to reduce the average size of a substantial portion of the biologically active compound particles or agglomerates by at least 25%. This method may be incorporated into a process for manufacturing a 10 biologically active compound formulation.

21 Claims, 8 Drawing Sheets

U.S. PATENT DOCUMENTS

| | | | | |
|---|---|---|---|---|
| 6,346,533 | B1 | 2/2002 | Cha et al. | |
| 6,410,935 | B1 | 6/2002 | Rajh et al. | |
| 6,497,905 | B1 | 12/2002 | Vladyka, Jr. et al. | |
| 7,384,560 | B2 * | 6/2008 | Martens et al. | 210/695 |

FOREIGN PATENT DOCUMENTS

| | | | |
|---|---|---|---|
| DE | 2 121 769 | | 12/1971 |
| EP | 0 326 143 | | 1/1989 |
| EP | 0 584 641 | | 8/1993 |
| EP | 0 949 217 | A1 | 10/1999 |
| GB | 1 004 570 | | 9/1965 |
| GB | 1 474 554 | | 5/1977 |
| GB | 2 065 157 | A | 6/1981 |
| JP | 50-116378 | | 9/1975 |
| JP | 11-151437 | | 6/1999 |
| JP | 2001348581 | | 12/2001 |
| JP | 2002-1390 | | 1/2002 |
| JP | 2006-285363 | | 10/2006 |
| WO | WO 97/07917 | | 3/1997 |
| WO | WO 03/072659 | | 9/2003 |
| WO | WO 2004/043580 | | 5/2004 |

OTHER PUBLICATIONS

Weiner, "Interactions Among Water Quality Parameters," *Applications of Environmental Chemistry*, Lewis Publishings, Chap. 3.1: 29-69 (2000).

International Preliminary Examination Report for PCT/BE03/00033, dated May 7, 2004.

International Search Report for PCT/BE03/00033, mailed on Aug. 6, 2003.

Kuznetsov et al., "Electromagnetic Grinding of Materials," Elektronnaya Orbrabotka Materioalov 3:39-41 (1976), Abstract.

Svalov et al., "Use of Magneto-Induction Effect," Izvestiya Vysshikh Uchebnykh Zavedenii, Gomyi Zhurnal 6:125-129 (1987), Abstract.

Voskanyan, R., "Tempering and Powder Particle Size Reduction-by Producing Random State Particles through Superimposing DC Magnetic Field on Alternating Magnetic Field," Ferment Product Res. (1978), Abstract.

PCT International Search Report (PCT/BE2004/000121), 2005.

PCT International preliminary Report on Patentability (PCT/BE2004/000121), 2005.

Written Opinion (PCT/BE2004/000121), 2005.

* cited by examiner

PARTICLE SIZE REDUCTION OF BIOACTIVE COMPOUNDS

CROSS-REFERENCE TO RELATED APPLICATIONS

This application is the U.S. National Stage of International Application No. PCT/BE2004/000121, filed Aug. 25, 2004, which in turn claims the benefit of GB Application No. 0319797.7, filed Aug. 26, 2003.

FIELD OF THE INVENTION

The invention relates to a method for the reduction of the size of solid drug particles in aqueous suspensions by conduction of the suspensions through magnetic fields, whereby the said particle size is reduced from the micrometer to the nanometer range. Furthermore, the invention relates to methods allowing the stabilisation of the obtained nano-particles as well as to formulations containing said stabilised nano-particles. The said formulations of the present invention are of particular relevance for the oral delivery of poorly soluble drug particles.

More generally, the present invention is in the field of the manufacture of particles of bioactive compounds of very small size. More specifically, the invention relates to the magnetic treatment of suspensions of particles of bioactive compounds. The invention also relates to methods of control of the particle average size and particle size distribution of the resulting particles. Finally the invention relates to pharmaceutical, phyto-pharmaceutical and veterinary products incorporating such small sized bioactive compound particles.

BACKGROUND OF THE INVENTION

The molecular structures of new chemical entities are becoming more complex leading to drugs with low aqueous solubility and dissolution rate limited absorption after oral administration, still the preferred route of drug administration. Considering the fact that many newly synthesized molecules are poorly soluble in aqueous environment, converting these compounds into useful therapeutics remains challenging. Techniques that have commonly been used to improve dissolution and bioavailability of poorly water-soluble drugs in general, include micronization, the use of surfactants, and the formation of solid dispersions.

Six types of drug-carrier interactions in solid state dispersions were already outlined in literature: simple eutectic mixtures, solid solutions, glass solutions, glass suspensions, amorphous precipitates in a crystalline carrier and compound or complex formation. Other factors such as increased wettability, solubilization of the drug by the carrier at the diffusion layer, and the reduction or absence of aggregation and agglomeration may also contribute to increased dissolution.

Drugs having a dissolution-limited oral absorption might benefit from a reduction in particle size, as pointed out in the following equation that is a modification of the well-known Noyes-Whitney relation:

where dM/dt is the dissolution rate, A the specific surface area of the drug $$\frac{dM}{dt} = \frac{AD(C_s - C_t)}{h}$$

particle, D the diffusion coefficient, h the diffusion layer thickness, $C_s$ the saturation solubility, and $C_t$ the drug concentration at time t. Since the surface area increases with decreasing particle size, higher dissolution rates may be achieved through the reduction of the particle size of drug substances. This effect has been highlighted by the superior dissolution rates after micronisation of certain sparingly water soluble drugs as opposed to regularly milled forms. However, particle size reduction does not necessarily always result in the expected improvement in dissolution rate. This effect arises as a result of the decrease of the effective surface area due to agglomeration and aggregation of very fine particles due to the increased surface energy and subsequent stronger van der Waals' attraction between non-polar molecules. Therefore, the surface of the particles needs to be protected from agglomeration.

U.S. Pat. No. 5,145,684 discloses particles consisting essentially of 99.9 to 10% by weight of a crystalline drug substance having a solubility in water of less than 10 mg/ml, said drug substance having a non-crosslinked surface modifier adsorbed an the surface thereof in an amount of 0.1 to 90% by weight and sufficient to maintain an effective average particle size of less than about 400 nm. In particular it discloses a modified steroid A aqueous dispersion, comprising 5% steroid A, with a particle size distribution ranging from about 68 to 520 nm and a number average particle size of 204 nm.

U.S. Pat. No. 5,503,723 discloses refining a nanoparticle dispersion by placing it between two electrodes and applying an electric field between said electrodes, wherein the dispersion consists essentially of particles of poorly soluble crystalline therapeutic or diagnostic agent, wherein 99% of the particles have a particle size below 400 nm and are associated with a surface modifier which is capable of stabilizing the nanoparticles. In particular, it describes a danazol dispersion wherein 10% of the particles are reduced in size down to 180 nm.

U.S. Pat. No. 5,858,410 discloses a drug carrier, prepared using the jet stream principle and using surfactants such as Tween 80 and mannitol, comprising particles of a therapeutic agent which is insoluble, only sparingly soluble or moderately soluble in water, aqueous media and/or organic solvents, wherein the therapeutic agent has an average diameter below 1,000 nm and the proportion of particles larger than 5 μm in the total population is less than 0.1%. In particular, it describes aqueous nanosuspensions comprising 2-15% of a substituted pteridine and at least 0.1% Tween 80 wherein the average particle diameter is in a range from 200 to 800 nm. It also teaches that for special tetracaine compositions with a low (1%) drug concentration, nanosuspensions with an average particle size of 91 nm may be obtained.

U.S. Pat. No. 5,922,355 discloses preparing microparticles of a water-insoluble or poorly soluble compound by, prior to or during reducing particle size (e.g. by sonication, homogenization, milling, microfluidization and precipitation, or recrystallization and antisolvent precipitation), mixing said particles with (a) a phospholipid and (b) at least one surfactant such that the concentration of phospholipid and surface modifier in the suspension or solid form is in the range of 0.1 to 50%, and thereafter applying energy to the mixture. It specifically describes drug formulations wherein the drug concentration is from 2 to 5%, wherein the mean particle size is between 35 and 98 nm and wherein there is no substantial variation in the mean particle size after one or more weeks storage of the formulations at 4° C.

U.S. Pat. No. 6,221,400 discloses nanocrystalline formulations of HIV protease inhibitors wherein the average particle size is below 400 nm. It specifically describes nanoparticulate compositions of indinavir wherein the mean size of the nanoparticles is between 127 and 267 nm.

International Patent application WO 02/055059 discloses methods involving both a water-miscible first solvent and an aqueous second solvent for preparing sub-micron sized particles of an organic compound. Using these methods, suspensions preparations wherein the average particle diameter is in the range from 180 to 700 nm.

Thus a common feature of the prior art publications is that it is extremely difficult to obtain drug suspensions wherein the average particle size is within the nanometer range, preferably below 500 nm. This was apparently achieved only in very specific drugs, provided further that the drug concentration in the suspension is low, e.g. below 5% by weight.

Because it is a sparingly water-soluble, normally crystalline active agent, itraconazole has attracted many attempts to improve its bioavailability. For instance, U.S. Pat. No. 6,346,533 discloses a method for obtaining itraconazole in an amorphous form exhibiting an improved bioavailability and having a particle diameter 0.5 to 10 μm. U.S. Pat. No. 6,497,905 discloses converting crystalline itraconazole into its amorphous form as a solid solution of a normally hydrophobic vehicle such as glyceryl monastearate, a monoglyceride, a diglyceride, a triglyceride, or a wax. This solid solution may be used as a component of a granular particle wherein itraconazole is present at about 5 to 60% by dry weight. Particle size of this granular particle is not specified.

International Patent application WO 2004/043580 discloses an emulsification method comprising flowing, conducting or circulating a pre-mix of two or more immiscible liquids, said pre-mix preferably comprising at least a hydrophilic liquid and at least a lipophilic liquid, through one or more magnetic fields under conditions to emulsify the said pre-mix. Although emulsions prepared according to this method may be included into veterinary or pharmaceutical compositions, this document does not refer to the solubilization of poorly soluble drugs as such.

There is a growing need in the art for improving the bioavailability in animals and in man for a number of bioactive compounds of various therapeutic groups because the water-solubility of these compounds is too low.

SUMMARY OF THE INVENTION

The present invention is based on the unexpected finding that a substantial portion of particles of a bioactive compound suspended in a fluid can be significantly reduced in size by flowing one or more times said fluid having a bioactive compound suspended therein through one or more magnetic fields. Another finding of this invention is that a number of bioactive compounds, especially poorly soluble drugs, being treated in this way show an improved bioavailability in animals and in man, both in vitro and in vivo.

DEFINITIONS

Figure 1:
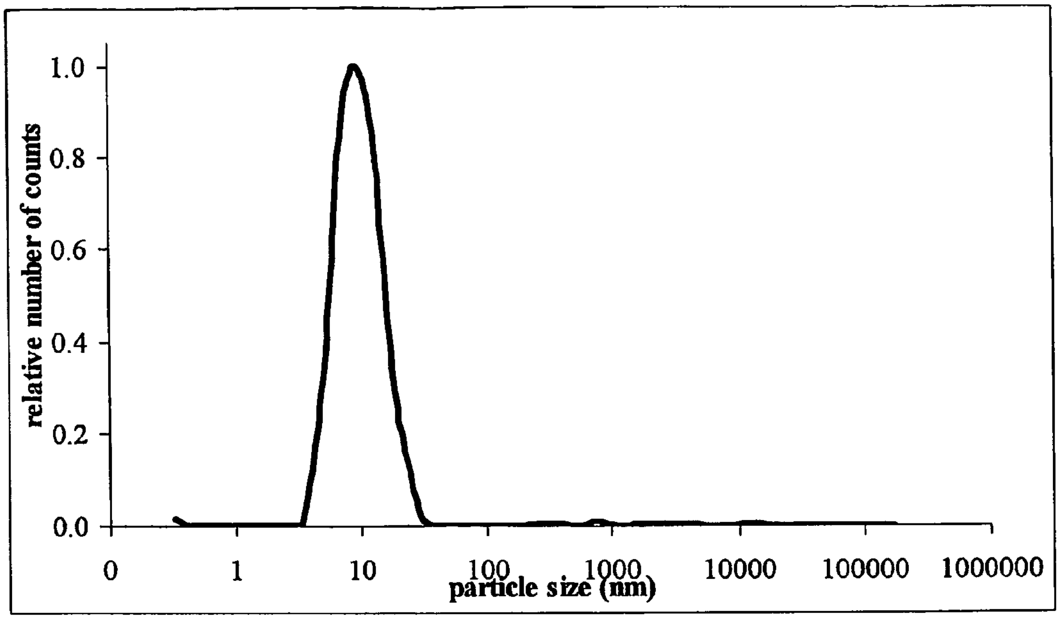
FIG. 1 represents the micelle size distribution of a Tween 80 surfactant in water as measured by dynamic light scattering.

The term "bioactive compound" as used herein refers to a chemical substance, preferably an organic substance, that acts upon or influences bodily functions of a human being, animal or plant in as far as said chemical substance does not comprise a metal ion and one or more atoms or groups of atoms, e.g. in the form of ionic bonds and/or ionic complexes.

The term "particles" as used herein refers to discrete individual units, such as but not limited to crystals, of a bioactive compound and being part of a population having an average size within a range usually between about 1 nanometer (nm) and about 10 μm, preferably between 0.45 μm and about 5 μm. The minimum average particle size of 0.45 μm refers to the nominal pore size of a filter used for filtering the total suspended solids (TSS) present in water, as explained by E. Weiner in *Applications of Environmental Chemistry* (2000), page 67.

The term "agglomerate" as used herein refers to an assembly of particles, being part of a population having an average size within a range usually between about 10 μm and about 100 μm.

The term "nanoparticles" as used herein refers to particles being part of a population having an average size below about 0.45 μm (450 nm), preferably within a range between 1 nm and about 450 nm.

The term "solid dispersion" as used herein refers to a product formed by converting a fluid drug-carrier combination to the solid state, e.g. see Corrigan in *Drug Dev. Ind. Pharm.* 11(1985) 697-724.

DETAILED DESCRIPTION OF THE INVENTION

In a first embodiment, this invention relates to a method and apparatus for reducing by at least about 25%, preferably at least about 50%, more preferably at least about 80%, the average size of a substantial portion of bioactive compound particles or agglomerates suspended in a fluid by flowing one or more times said fluid having bioactive compound particles or agglomerates suspended therein through one or more magnetic fields. The present invention also provides an apparatus for reducing the average size of a substantial portion of bioactive compound particles or agglomerates suspended in a fluid, said apparatus comprising: a source of bioactive compound particles or agglomerates suspended in a fluid, means for generating one or more magnetic fields, and means for flowing said fluid having bioactive compound particles or agglomerates suspended therein one or more times through the one or more magnetic fields. A means for measuring a turbidity of the fluid with bioactive compound particles or agglomerates suspended therein may be included in said apparatus, for the purpose of process control if necessary. A means for measuring a particle size of bioactive compound particles or agglomerates suspended in the fluid may also be provided with said apparatus, for the purpose of alternative process control if necessary.

According to the method of the invention, it should be understood that the effect of the method on the average size of particles or agglomerates is significantly more important when the strength of the magnetic field is higher and/or when the number of flows through the said magnetic field is higher. Since the strength of each commercially available magnet is usually limited to about 10,000 gauss, a means to increase the effective magnetic field is to flow the suspension through a number of magnetic devices arranged in series (especially for limiting the duration of treatment) and/or to recirculate the suspension several times through the same magnetic fields. Preferably the strength of each said magnetic field used for carrying out the method of the invention is at least about 2,000 gauss.

The bioactive compound present in the particles or agglomerates to be magnetically treated according to this invention may be selected from a very wide range of species. In general, the compounds used as pharmaceutical, veterinary or phyto-pharmaceutical agents are organic substances. Therefore, in a preferred embodiment, the present invention relates to the magnetic treatment of organic bioactive compounds. The method of the present invention is particularly useful in the preparation of drug delivery formulations suitable for the oral administration of a bioactive compound, especially one having a low solubility and/or a low dissolution rate, to an animal or human being in need thereof. Typically, drugs having a dissolution-limited oral absorption are classified as Class II or Class IV compounds in the Biopharmaceutical Classification System (hereinafter referred as BCS). The BCS according to G. Amidon et al. in *Pharm. Res.* (1995) 12:413-420 provides for two classes of poorly soluble drugs, i.e. Class II and Class IV, and two classes of highly soluble drugs, i.e. Class I and Class III. According to M. Martinez et al., Applying the Biopharmaceutical Classification System to Veterinary Pharmaceutical Products (Part I: Biopharmaceutics and Formulation Consideration) in *Advanced Drug Delivery Reviews* (2002) 54:805-824, a drug substance should be classified as highly soluble when the highest dose strength is soluble in at most 250 ml of aqueous media over the pH range 1-7.5. Amongst others, bioactive compounds of which the bioavailability may be improved by formulating said compounds using the method of the present invention include the following: acetylsalicylic acid, amprenavir, anipamil, bentezone, benzocaine, benzafibrate, bexarotene, biperiden, butazolidin, captopril, carbamazepine, chloramphenicol, clofazimine, cromoglicic acid, clotrimazole, caffeine, cyclosporin, diazepam, diclofenac, digoxin, dilliazon, diltiazem, dimetridazole, diphenhydramine, 5,5-diphenylhydantoin, dronabinol, dutasteride, etoposide, erythromycin stearate, esuprone, fenofibrate, flecainide, furosemide, fluconazole, gallopamil, glibenclamide, griseofulvin, hydrochlorothiazide, ibuprofen, indometacin, (iso)tretinoine, itraconazole, ketoconazole, ketoprofen, loperamide, lopinavir, melperone, metazachlor, nalixidic acid, naftidrofuryl, nexopamil, nifedipine, nimodipine, nitrendipine, nitrofurantoin, oxybutynin, paracetamol, pentoxifylline, paroxetine, prazosin, propafenone, progesterone, pseudoephedrine, ranitidine, riboflavin, risperidone, ritonavir, saquinavir, sirolimus, selegiline, sulfamethazine, sulfamethoxazole, sulfathiazole, spirinolactone, tacrolimus, theophylline, tolbutamide, triamterene, trimethoprim, valproic acid and zotepine. Drugs or bioactive compounds that may be treated according to this invention preferably have a water-solubility below about 2.5 mg/ml, even between 0.1 and 1 mg/ml (i.e. “very slightly soluble” as defined in the United States Pharmacopeia), even below 0.1 mg/ml (i.e. “practically insoluble” as defined in the United States Pharmacopeia), even below about 5 μg/ml and may even have a water-solubility as low as about 0.2 μg/ml, at room temperature and physiological pH. Non-limiting examples of such drugs include for instance chlorothiazide, hydrochlorothiazide, nimodipine, flufenamic acid, furosemide, mefenamic acid, bendroflumethiazide, benzthiazide, ethacrinic acid, nitrendipine, itraconazole, saperconazole, troglitazone, prazosin, atovaquone, danazol, glibenclamide, griseofulvin, ketoconazole, carbamazepine, sulfadiazine, florfenicol, acetohexamide, ajamaline, benzbromarone, benzyl benzoate, betamethasone, chloramphenicol, chlorpropamide, chlorthalidone, clofibrate, diazepam, dicumarol, digitoxin, ethotoin, glutethimide, hydrocortisone, hydroflumethiazide, hydroquinine, indomethacin, ibuprofen, ketoprofen, naproxen, khellin, nitrazepam, nitrofurantoin, novalgin, oxazepam, papaverine, phenylbutazone, phenyloin, prednisolone, prednisone, reserpine, spironolactone, sulfabenzamide, sulfadimethoxine, sulfamerazine, sulfamethazine, sulfamethoxypyridazine, succinylsulfathiazole, sulfamethizole, sulfamethoxazole (also in admixture with trimethoprim), sulfaphenazole, sulfathiazole, sulfisoxazole, sulpiride, testosterone and diaminopyrimidines. Suitable examples of diaminopyrimidines include, without limitation, 2,4 diamino-5-(3,4,5-trimethoxybenzyl) pyrimidine (known as trimethoprim), 2,4-diamino-5-(3,4-dimethoxybenzyl) pyrimidine (known as diaveridine), 2,4 diamino-5-(3,4,6-trimethoxybenzyl) pyrmidine, 2,4-diamino-5-(2-methyl-4,5-dimethoxybenzyl) pyrimidine (known as ormetoprim), 2,4-diamino-5-(3,4-dimethoxy-5-bromobenzyl) pyrimidine, and 2,4-diamino-5-(4-chloro-phenyl)-6-ethylpyrimidine (known as pyrimethamine). As will be appreciated by those skilled in the art, these drugs belong to various therapeutic classes, including diuretics, anti-hypertensive agents, anti-viral agents, antibacterial agents, antifungals, etc, and are not limited to human or veterinary use alone. The bioactive compound may also be a cosmetic agent, a diagnostic agent, a herbicide, an insecticide, a biocide or a fungicide. Among the more recently developed drugs, proteins and peptides represent an important part. These compounds are often poorly permeable, poorly soluble, unstable in physiological fluids, with rapid drug metabolism in vivo and unfavourable pharmacokinetics. Therefore, the method of the present invention may also prove useful for the preparation of delivery forms for the administration of protein and peptide drugs.

When the method of the invention is performed on bioactive compound agglomerates (such as above defined), the average size of a substantial portion of said bioactive compound agglomerates may be reduced to a range from about 0.45 μm to 5 μm and/or the said substantial portion of agglomerates with reduced size is at least about 50% by weight of the suspended agglomerates. When the method of the invention is performed on bioactive compound particles (such as above defined), the average particle size of said bioactive compound particles may be reduced to a range from about 0.5 nm to about 500 nm, preferably from 1 to 300 nm, more preferably from 5 to 200 nm, most preferably from 5 to 100 nm and/or the said substantial portion of particles with reduced size is at least about 10% by weight, preferably at least 20% by weight of the suspended particles. The skilled person understands that the extent to which the size of bioactive compound particles or agglomerates is reduced depends not only upon the magnetic field strength and the duration of treatment of the suspension including such particles or agglomerates, but also upon other parameters such as, but not limited to, the nature (in particular the ionic binding character and dipole strength) of the bioactive compound, the flow rate of the fluid wherein the bioactive compound particles or agglomerates are suspended, the concentration of such particles or agglomerates in said fluid, the physical and chemical conditions (including pH) during treatment, the crystalline form or geometrical shape of the particles, the presence of optional other components in or together with said particles or agglomerates, and so on. All such parameters will now be discussed into further details, being understood that the following teachings allow the skilled person to perform certain variations to each parameter and certain combinations of parameters for achieving the goals of the invention without undue experimental burden.

Preferably the fluid wherein the bioactive compound particles or agglomerates are suspended is a liquid under the temperature and pressure conditions prevailing during the magnetic treatment of the invention. More preferably the said fluid is water, although the said fluid may also be an organic solvent, for instance selected from the group consisting of alcohols, esters, ethers, ketones, amides or mixtures thereof, or a combination of such organic solvent(s) with water. There is no particular restriction upon the choice of the particular fluid of interest, which may be adapted to the usual conditions prevailing in the application for which there is a need to significantly reduce the size of bioactive compound particles or agglomerates involved. Important is that said bioactive compound particles or agglomerates are substantially suspended, not dissolved, in the said fluid, i.e. preferably suspended in the form of a slurry wherein the concentration of said bioactive compound particles or agglomerates in said fluid is at least 1.05 times, preferably at least 2 times, the solubility limit of said bioactive compound in said fluid under the physical (temperature, pressure) and chemical (pH) conditions prevailing while flowing said slurry through the magnetic field(s). The solubility limit of a certain bioactive compound in a certain fluid is a parameter which is either readily available in the literature or which may be easily determined by the skilled person by using techniques well known in the art. It is well known that the solubility limit may be heavily dependent upon temperature and pH, therefore it should first be carefully determined when the literature is silent about its value upon specific temperature and pH conditions. For obvious practical reasons, the upper concentration of the bioactive compound particles or agglomerates in the fluid, when the fluid is a liquid, is determined by the necessity to flow the said fluid through the magnetic field(s) at an effective linear flow rate, i.e. is determined by the viscosity of the fluid suspension.

For certain special applications, the fluid wherein the bioactive compound particles or agglomerates are suspended may also be a gas or a supercritical fluid (e.g. carbon dioxide). The nature of the said gas or critical fluid may widely depend upon the chemical constitution and reactivity of the bioactive compound.

Whatever the fluid, flowing said fluid through the magnetic field(s) is preferably effected at a temperature below half of the Curie temperature of the magnetic material used for generating said magnetic field(s), e.g. below about 400° C. for a magnetic device of the Al—Ni—Co type (as is well known to the skilled person, the Curie temperature depends upon the exact composition of the alloy). When the fluid wherein the bioactive compound particles or agglomerates are suspended is a liquid, flowing said liquid through said magnetic field(s) is preferably effected at a temperature between the freezing temperature and the boiling temperature of said fluid under the pressure prevailing while flowing said fluid through said magnetic field(s). For instance when said fluid is water under atmospheric pressure, flowing said liquid through said magnetic field(s) is preferably effected at a temperature between about 2° C. and 95° C.

The bioactive compound particles submitted to the size reduction treatment of this invention may be of any geometrical shape or crystalline form such as, but not limited to, spherical particles or prismatic particles, as well as cubic, tetragonal, hexagonal and octahedral structures.

For certain applications, it may be advantageous to carry out the method of this invention in such a way that the liquid wherein the bioactive compound particles or agglomerates are suspended includes one or more stabilising agents to prevent the re-agglomeration and re-aggregation of the size-reduced particles or agglomerates. Such stabilising agent can either be a surfactant, a polymer, a hydrophilic material, a silicate or a combination thereof. Since at least traces of said stabilising agents may remain present in the final pharmaceutical or veterinary delivery form, the stabilising agents should preferably be pharmaceutically acceptable excipients. Hydrophilic materials suitable for this purpose can be selected from the non-limiting list of compounds such as glucose, fructose, lactose, sorbitol, xylitol, manitol and starch, amongst others. Polymers suitable for this purpose can be selected from the non-limiting list of cellulose derivatives (e.g. hydroxy propyl cellulose, methyl cellulose, carboxymethyl cellulose, sodium or calcium carboxymethyl cellulose, hydroxyethyl cellulose, microcrystalline cellulose, hydroxy propyl methyl cellulose, hydroxy propyl methyl cellulose phtalate, cellulose acetate phtalate), albumin, alginic acid, sodium alginate, polymethacrylates, polyacrylic acid, polyacrylates, cyclodextrins and derivatives thereof, tragacanth, acacia gum, gelatin, pectine, guar gum, xanthan gum, polyvinylpyrrolidon, polyvinylpyrrolidone-co-vinylacetate, polyethyleneglycol, copolymers of ethylene oxide and propylene oxide, polyvinylalcohol and the like. Suitable surfactants can be selected from the group consisting of cetostearyl alcohol, cetyl alcohol, cetrimide, sodium docusate, mono glycerides, diglycerides, lecithine, taurocholates, polyoxyethylene alkyl ethers, polyoxyethylene castor oil derivatives, polyoxyethylene sorbitan fatty acid esters, polyoxyehtylene stearates, sodium lauryl sulfate, sorbitan fatty acid esters, stearyl alcohol and the like, and mixtures thereof.

Preferably the method according to the invention involves re-circulating (e.g. in a closed circuit) two or more times the fluid wherein the bioactive compound particles or agglomerates are suspended through the magnetic field(s). The number of re-circulation times may be easily adapted to the specific average size targeted for the specific bioactive compound involved in a certain application. It is important that the fluid wherein the bioactive compound particles or agglomerates are suspended is flowed or circulated through the magnetic field(s) at a speed which allows the magnetic treatment to effectively perform the size reduction to a significant extent. Preferably, the linear flow rate of said fluid through each said magnetic field is between about 0.25 and 25 m/s. In view of the length of the magnetic field, it may be calculated that the residence time of said fluid through each said magnetic field is preferably between about 60 microseconds and 10 seconds, depending upon the number or re-circulation times.

A usual consequence of the magnetic treatment of the invention is that the turbidity of the suspension of said bioactive compound particles is altered. Depending upon the population of particles or agglomerates (whether large or medium-size) that is more concerned by size reduction and the extent to which such size reduction occurs, turbidity may be reduced or increased, as can be estimated or measured by means of turbidimeters well known in the art. Therefore turbidity can be used as an additional property in order to characterise the resulting particle suspension, as will be described in the following other embodiments of this invention.

In another embodiment, the present invention also provides a process involving the use of bioactive compound particles or agglomerates, comprising a step of reducing by at least 25%, preferably at least 50%, more preferably at least 80%, the average size of a substantial portion of said bioactive compound particles or agglomerates, wherein said step includes a method as described with respect to the first embodiment of the invention. Such a process may further comprise one or more post-processing steps performed following the size reducing step.

Said post-processing step may be a heating step. In another example, said post-processing step may be a drying step for substantially removing the fluid in which the bioactive compound particles or agglomerates are suspended during the size reducing step. Such drying step, which can be performed by any known drying techniques, may be required for providing dried smaller particles to a subsequent step of the said process. In a preferred embodiment said process comprises a freeze-drying step. A particular example of this variant of the third embodiment is a process for the preparation of a solid dispersion of a bioactive compound comprising the steps of: (i) preparing a suspension comprising particles and/or agglomerates of a bioactive compound and one or more stabilising agents, (ii) flowing said suspension through one or more magnetic fields, (iii) instantaneous freezing of this mixture and (iv) freeze drying of the preparation to obtain a solid dispersion. In another preferred embodiment said process comprises a spray-drying step. A particular example of this variant of the third embodiment is a process for the preparation of a solid dispersion of a bioactive compound comprising the steps of: (i) preparing a suspension comprising particles particles and/or agglomerates of a bioactive compound and one or more stabilising agents, (ii) flowing said suspension through one or more magnetic fields, (iii) spray-drying of the preparation to obtain a solid dispersion. Alternatively, after magnetic treatment the suspension can be spray-coated on pharmaceutical pellets (for example inert sugar spheres), these coated pellets can thereafter be formulated into capsules or other solid dosage forms such as tablets.

In another variant of this embodiment of the invention, the post-processing step may be a step of mixing one or more adjuvants or additives together with the optionally dried particles or agglomerates with reduced size. Mixing such kind of adjuvant or additive may be performed by ball milling or other mixing techniques well known to the skilled person.

In yet another variant of this embodiment of the invention, the post-processing step may be a step of diluting the suspension of bioactive compound particles or agglomerates with reduced size through the addition of a fluid into said suspension. For instance, the fluid used in said diluting step may be miscible with (e.g. the same as) the fluid present in the size reduction step.

For quality control purpose, the process of this embodiment of the invention may further comprise one or more steps of controlling the size of bioactive compound particles or agglomerates produced during or after the magnetic treatment method, i.e. the method constituting the first embodiment of the invention. In view of the order of magnitude of the particle sizes involved, said size controlling step is preferably performed by dynamic light scattering analysis. When said process comprises a post-processing step performed following the size reduction step, it may further comprise one or more steps of controlling the size of bioactive compound particles or agglomerates produced during or after said post-processing step, in which case said size controlling step after said post-processing step may be performed by dynamic light scattering analysis. The size controlling step may be performed in such a way as to; measure the average size and/or the size distribution of the particles produced during the various steps of said process. In yet another variant of the third embodiment of the invention, the post-processing step may be a sonication step.

For quality control purpose, the process according to this embodiment of the invention may further comprises one or more steps of controlling the turbidity of the suspension of bioactive compound particles or agglomerates involved in said process. This turbidity controlling step may be suitably performed by means of any type or turbidimeter available to those skilled in the art.

The invention also relates to populations of certain bioactive compounds, such as above described, with an average particle size between about 1 nm and about 40 nm, preferably between about 2 nm and about 20 nm, more between about 3 nm and about 15 nm, and/or with a narrow particle size distribution (e.g. a polydispersity from about 1.1 to about 4.0, preferably from about 1.2 to about 3.0, more preferably from about 1.3 to about 2.0), namely with respect to bioactive compounds which have never been able to be produced in such small particle sizes and/or such narrow particle size distribution. Such bioactive compound particle populations may be isolated from the particles obtainable from the magnetic treatment of the invention by performing, after said magnetic treatment, a separation step by means of techniques well known in the art, such as ultra-centrifugation, ultra-filtration or nano-filtration, e.g. with the aid of permeable membranes.

The bioactive compound may be treated as such or as formulations of said biologically active ingredients (e.g. drugs) which further comprise one or more physiologically (e.g. pharmaceutically) acceptable excipients, such as emulsifiers or surface-active agents, thickening agents, gelling agents or other additives, and wherein the active ingredient (e.g. drug) loading, i.e. the proportion or content of the active ingredient (e.g. drug) in the formulation, may vary through wide ranges. For instance said active ingredient content may be at least about 0.1% by weight, preferably at least 1% by weight, more preferably at least 5% by weight. Furthermore, said active ingredient content may be at most about 99% by weight, preferably at most 95% by weight, more preferably at most 50% by weight.

Emulsifiers or surface-active agents suitable for therapeutically active formulations or detergent compositions include water-soluble natural soaps and water-soluble synthetic surface-active agents. Suitable soaps include alkaline or alkaline-earth metal salts, unsubstituted or substituted ammonium salts of higher, preferably saturated, fatty acids ($C_{10}$-$C_{22}$), e.g. the sodium or potassium salts of oleic or stearic acid, or of natural fatty acid mixtures obtainable form coconut oil, palm oil or tallow oil. Synthetic surface-active agents (surfactants) include anionic, cationic and non-ionic surfactants, e.g. sodium or calcium salts of polyacrylic acid; sulphonated benzimidazole derivatives preferably containing 8 to 22 carbon atoms; alkylarylsulphonates; and fatty sulphonates or sulphates, usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide) and the like.

Suitable emulsifiers further include partial esters of fatty acids (e.g. lauric, palmitic, stearic or oleic) or hexitol anhydrides (e.g., hexitans and hexides) derived from sorbitol, such as commercially available polysorbates. Other emulsifiers which may be used include, but are not limited to, adducts of polyoxyethylene chains (1 to 40 moles ethylene oxide) with non-esterified hydroxyl groups of the above partial esters, such as surfactants commercially available under the trade name Tween from ICI Americas Inc.; and the poly(oxyethylene)/poly(oxypropylene) materials marketed by BASF under the trade name Pluronic.

Suitable structure-forming, thickening or gel-forming agents for the biologically active formulation of the invention include highly dispersed silicate, such as the product commercially available under the trade name Aerosil; bentonites; tetraalkyl ammonium salts of montmorillonites (e.g. products commercially available under the trade name Bentone) wherein each of the alkyl groups may contain from 1 to 20 carbon atoms; cetostearyl alcohol and modified castor oil products (e.g. a product commercially available under the trade name Antisettle).

Gelling agents which may be included into the biologically active ingredient formulations of the present invention include, but are not limited to, cellulose derivatives such as carboxymethylcellulose, cellulose acetate and the like; natural gums such as arabic gum, xanthum gum, tragacanth gum, guar gum and the like; gelatin; silicium dioxide; synthetic polymers such as carbomers, and mixtures thereof. Gelatin and modified celluloses represent a preferred class of gelling agents.

Hydrophilic cellulose derivatives may be used as well as pharmaceutically acceptable excipients for the formulations of therapeutically active ingredients according to the invention. The term "hydrophilic" herein refers to a cellulose derivative or polymer having groups, preferably non-ionizable groups, that are capable of hydrogen bonding, in particular of association with water molecules at physiologically relevant pH. Suitable examples of hydrophilic cellulose polymers that can be used in the present invention include polymers having ether-linked substituents, for instance hydroxyalkylalkylcelluloses (wherein the alkyl group preferably has from 1 to 4 carbon atoms) such as hydroxypropylmethylcellulose. Hydroxypropylmethylcellulose is cellulose 2-hydroxypropyl methyl ether (hereinafter referred to as HPMC). It is a non-ionic water-soluble ether of methylcellulose which is insoluble in hot water but dissolves slowly in cold water. Being used extensively as a drug tablet excipient, HPMC is commercially available under various trade names. Suitable grades of HPMC include a low viscosity grade such as Methocel K100 from Dow Chemical, a high viscosity grade such as Methocel K100M, and other types such as the Metolose 90SH series from Shinetsu.

Amphiphilic materials may be used as well as pharmaceutically acceptable excipients for the formulations of therapeutically active ingredients according to the invention. The term "amphiphilic" herein refers to a material having both a hydrophobic portion, for instance comprising aliphatic or aromatic hydrocarbon groups, and a hydrophilic portion. Suitable examples of such amphiphilic materials include those having both a portion derived from a glyceride and a portion derived from a polyethylene glycol ester. For instance, it is suitable to use polyglycosylated glycerides as an amphiphilic material excipient in the present invention. The expression "polyglycosylated glycerides" as used herein denotes a mixture of mono-, di- and triglycerides with polyethylene glycol (PEG) mono- and diesters of $C_8$-$C_{18}$ fatty acids with a molecular weight preferably between about 200 and about 600, optionally further including glycerol and/or free PEG, the hydrophilic-lipophilic balance (HLB) value of which is controlled by the chain length of the PEG and the melting point of which is controlled by the chain length of the fatty acids, of the PEG and of the degrees of saturation of the fatty chains, and thus of the starting oil. Similarly the expression "$C_8$-$C_{18}$ fatty acids" as used herein denotes mixtures in various proportions of caprylic acid, capric acid, lauric acid, myristic acid, palmitic acid and stearic acid, when these acids are saturated, and the corresponding unsaturated acids. As is well known to the skilled person, the proportions of these fatty acids may vary as a function of the starting oils. Examples of the latter include, but are not limited to, saturated polyglycolized $C_8$-$C_{10}$ glycerides, such as the PEG-8 caprylate-caprate glyceride esters sold by Gattefosse Corporation under the tradename Labrasol; PEG-6 caprylic/capric glycerides sold by Huls Aktiengesellschaft under the trade name Softigen 767; PEG-60 corn glycerides sold by Croda under the trade name Crovol M-70; Ceteareth-20 sold by Henkel Corporation under the trade name Eumulgin B2; diethyleneglycol monoethyl-ethers sold by Gattefosse Corporation under the trade name Transcutol; a mixture of $C_8$-$C_{18}$ saturated polyglycosylated glycerides having a melting point within a range of about 42-48° C. and a HLB within a range of about 8 to 16 such as sold by Gattefosse Corporation under the trade names Gelucire 48/09, Gelucire 44/14 and Gelucire 42/12; and mixtures thereof in various proportions.

Other optional excipients which may be present in the biologically active formulations according to the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetra-acetic acid; flavoring agents such as natural vanillin; buffers such as citric acid or acetic acid; extenders or bulking agents such as silicates, diatomaceous earth, magnesium oxide or aluminum oxide; densification agents such as magnesium salts; and mixtures thereof.

When the biologically active formulation is intended for making effervescent granules, it should necessarily include sodium bicarbonate and one or more weak acids, such as citric acid or tartaric acid, acting as a carbon dioxide liberator.

Such effervescent granules can be made for the purpose of effervescent tablets, e.g. for cleaning artificial teeth.

The selection of the optimal excipients and their proportion in the biologically active formulations of the present invention depends, in a manner which is well known to the skilled person, on a series of parameters such as, but not limited to, the specific biologically-active ingredient to be formulated, the end-user requirements, the load (i.e. weight proportion) of the biologically-active ingredient and the required biologically-active ingredient (e.g. drug) release characteristics (in particular kinetics).

The present invention shows a number of advantages over the methods of the prior art. Firstly, this size reduction is achieved by means of inexpensive readily available magnetic devices of any type, which may be combined in a number of ways for fine tuning the extent of size reduction that is targeted. Secondly it achieves substantial size reduction of particles and agglomerates of a huge number of bioactive compounds, especially bioactive compounds comprising a dipole.

The following examples are provided for illustration purposes only and should in no way be interpreted as limiting the scope of the present invention.

EXAMPLE 1

48 mg of Tween 80 (commercially available from Imperial Chemical Industries plc, London, UK) was mixed with 20 ml of bi-distilled water and stirred for a few minutes at 100 rpm with a magnetic bar stirrer. Tween micelles were sized by means of dynamic light scattering (hereinafter referred as DLS) using a He—Ne high performance particle sizer (2.5 mW) commercially available from ALV (Germany). FIG. 1 shows that Tween 80 organises itself in water into micelles with a mean diameter of about 10 nm.

EXAMPLE 2

50 mg of diazepam (commercially available from Alpha Pharma NV, Zwevegem, Belgium) and 48 mg of Tween 80 (same as in example 1) were crushed in a mortar. 150 ml of bi-distilled water was added and the suspension was sonicated for 20 minutes. After sonication the suspension was continuously stirred with a magnetic stirrer at 600 rpm until further use.

Figure 2:
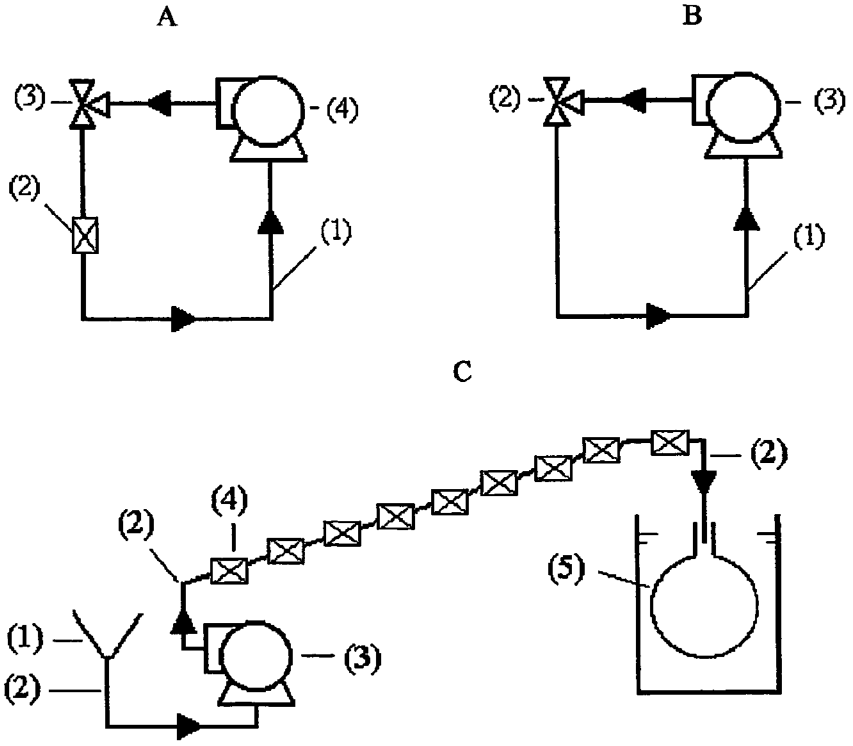
FIG. 2 shows three schematic set-ups of an apparatus for performing an embodiment of the method of this invention.

Magnetic treatment was performed in a closed system shown in FIG. 2A, having a total volume of 100 ml and consisting of (1) a tubing (Masterflex Tygon lab I/P 70, Cole-Parmer Instrument Company, Illinois, USA), (2) an internal magnet of the Al—Ni—Co type, (W, SAN R1/4D, CEPI-CO, Borgerhout, Belgium), (3) a 3-way horizontal ball valve (Georg Fischer Rohrleitungs-systeme AG, type 343 DN10/15, Schaffhausen, Switzerland) and (4) a pump (Masterflex I/P, Cole-Parmer Instrument Company, Illinois, USA). The pump was operated at a flow rate of 4.7 l/min, equaling a velocity of 11 m/sec through the magnetic field and a residence time in the field of 136 μs per pass through the device. Part of the diazepam suspension was introduced in the closed system and was re-circulated through the magnetic field.

Figure 3:
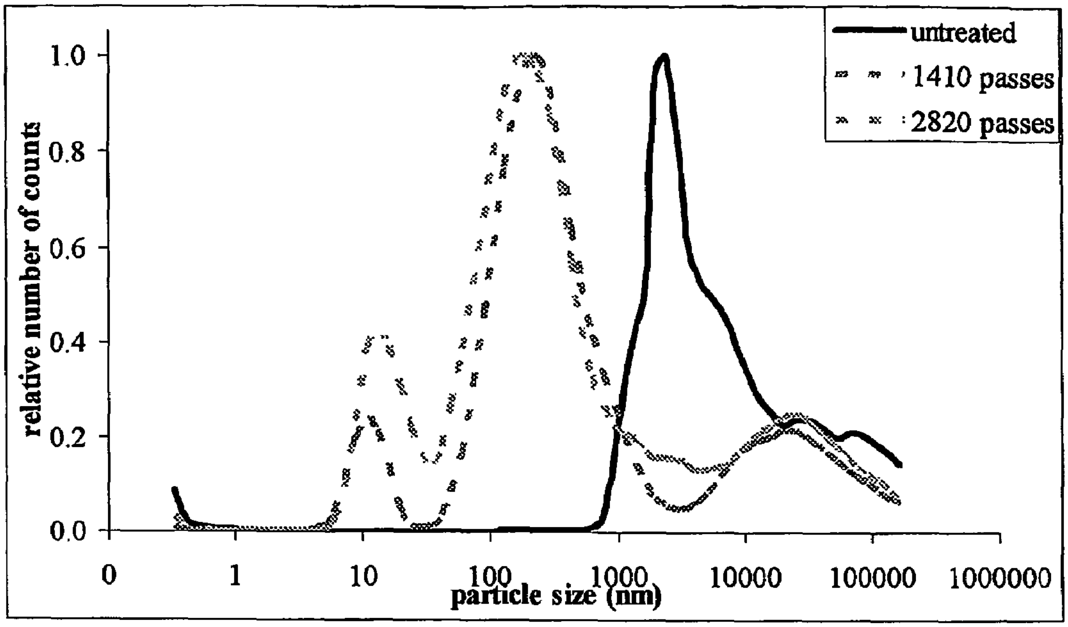
FIG. 3 shows the particle size distribution of two magnetically treated diazepam samples compared to an untreated reference sample.

After 30 and 60 minutes of treatment, corresponding to 1,410 and 2,820 recirculations (passes) through the magnetic field respectively, samples were taken. Immediately after sampling DLS measurements were performed. The samples were shaken before placing them in the particle sizer. FIG. 3 compares the particle size distribution of the diazepam dispersion before and after magnetic treatment. FIG. 3 shows that both magnetically treated samples have significant amounts of particles smaller than 1 μm, with major populations centered around the 11-13 nm range and around the 200-250 nm range. The untreated reference sample contains very few particles below 1 μm and a major population occurrence may be seen at 2.5 μm. Particles with a size about 10 nm are very likely related to the presence of Tween micelles (based on the teaching of example 1).

Figure 4:
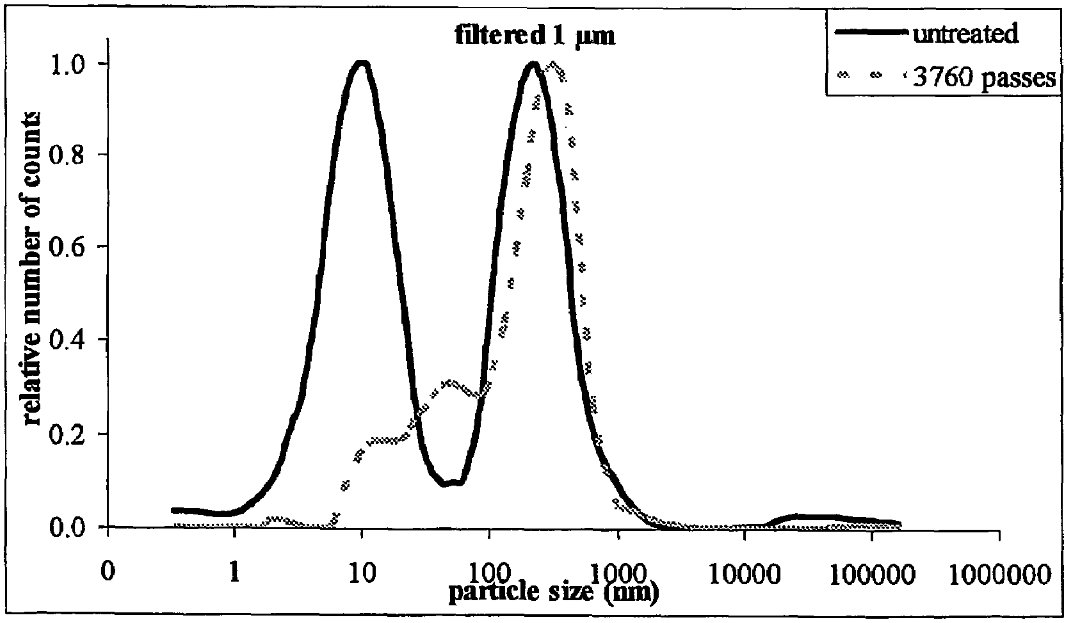
FIG. 4 shows the particle size distribution of a magnetically treated diazepam sample compared to an untreated reference sample after filtration.

After 80 minutes of treatment corresponding to 3,760 re-circulations (passes), a third sample was taken. This sample was filtered over a Puradisc 25 AS disposable filter with a polysulfone membrane (commercially available from Whatman International LTD., Maidstone, England) having a pore size of 1 μm. Thereafter, DLS measurements were performed on the resulting filtrate and the particle size distributions were compared with the filtrate of the untreated dispersion in FIG. 4. The particle size distribution of the magnetically treated suspensions is similar with (FIG. 4) and without filtration (FIG. 3). The filtrate of the untreated suspension contains Tween micelles (peak at 11 nm) and 200 nm diazepam particles (FIG. 4). These observations were not revealed when analysing the unfiltered, untreated suspension (FIG. 3) because their presence was masked by the abundance of particles larger than 1 μm. It may thus be concluded that the micrometer sized particles in the untreated dispersion were broken down into nanometer sized particles by the magnetic treatment of the invention.

EXAMPLE 3

2 g/l of diazepam (commercially available from Alpha Pharma NV, Zwevegem, Belgium) and 2 g/l of Tween 80 (same as example 1) were mixed with bi-distilled water in a mortar. The resulting suspension was poured in a beaker and sonicated during 20 minutes and afterwards continuously stirred at 600 rpm using a magnetic stirrer until further use.

Part of the suspension was subjected to magnetic treatment in a closed system (FIG. 2A) similar to the one used in example 2, but with a total volume of 150 ml. After 90 minutes of treatment at 4.7 l/minute, corresponding to 2,820 re-circulations through the magnetic field, a magnetically treated sample was collected for filtration. A second part of the suspension was treated in a 150 ml closed system lacking the internal magnetic device (FIG. 2B). After 90 minutes of operation at 4.7 l/minute, corresponding to 2,820 re-circulations, a blank re-circulated sample was collected for filtration. A third part of the initial suspension was continuously stirred with a magnetic stirrer at 600 rpm for 1 hour (untreated reference sample).

ProFill syringe filters with polytetrafluoroethylene (hereinafter PTFE) and a pore size of 0.45 μm (commercially available from Alltech Associates Inc., Illinois, United States) were washed with bi-distilled water and dried for 12 hours at 70° C. ProFill syringe filters with PTFE and a pore size of 0.2 μm (Alltech Associates Inc., Illinois, USA) were not washed nor dried. 40 ml of suspension was filtered, the filtrate was poured into a Petri dish and both the filter and the Petri dish were dried for 48 hours at 70° C. This experiment was performed with magnetically treated, blank re-circulated and untreated suspension, with both types of filters. After drying, the amounts of solid matter present in the Petri dishes and on the filters were quantified for each experiment. Table 1 below represents the amount of material retained by the filter as a percentage of the total dry mass.

TABLE 1

| sample | filter | Amount retained (%) |
|---|---|---|
| Untreated reference | 450 nm | 48 |
| Untreated reference | 200 nm | 47 |
| Blank recirculated | 450 nm | 16 |
| Blank recirculated | 200 nm | 21 |
| Magnetically treated | 450 nm | 5 |
| Magnetically treated | 200 nm | 8 |

Assuming that no surfactant (Tween 80) was retained during filtration, it can be concluded that almost all diazepam (94 to 96%) is retained by both the 450 nm and 200 nm filters in the untreated reference sample. In the blank recirculated sample 32% of diazepam is larger than 450 nm and 42% is larger than 200 nm. In the magnetically treated sample on the other hand only 10% of diazepam is larger than 450 nm and 16% is larger than 200 nm. This clearly illustrates the beneficial effect of magnetic treatment on the particle dimensions. The fact that less diazepam was retained on the filters in the blank recirculated sample than in the untreated sample may be explained by a number of factors comprising increased solubility (e.g. due to heat generated by the pump), abrasion of particles in contact with the closed system, etc.

EXAMPLE 4

Figure 5:
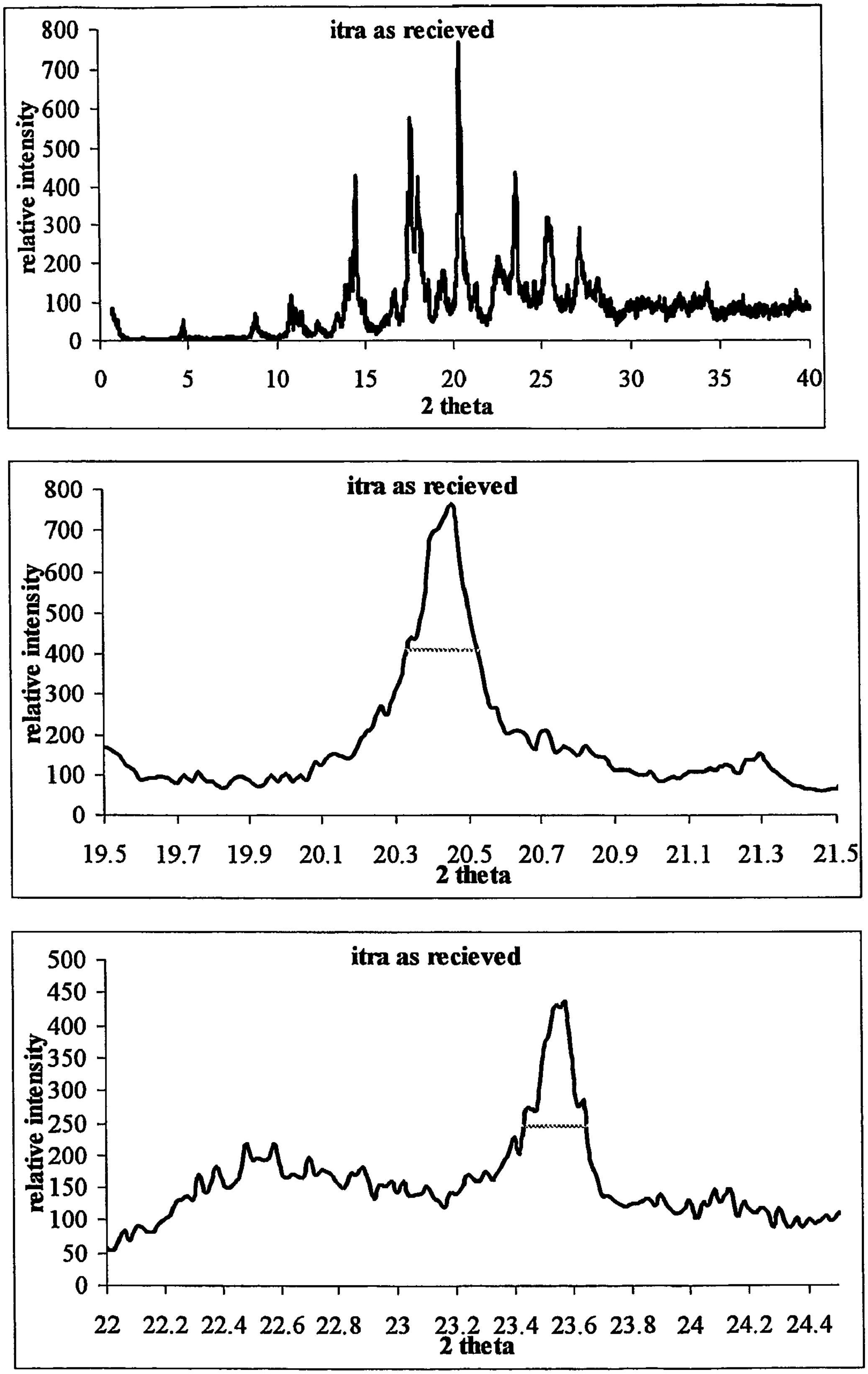
FIG. 5 shows the X-ray diffraction pattern of untreated crystalline itraconazole.
Figure 6:
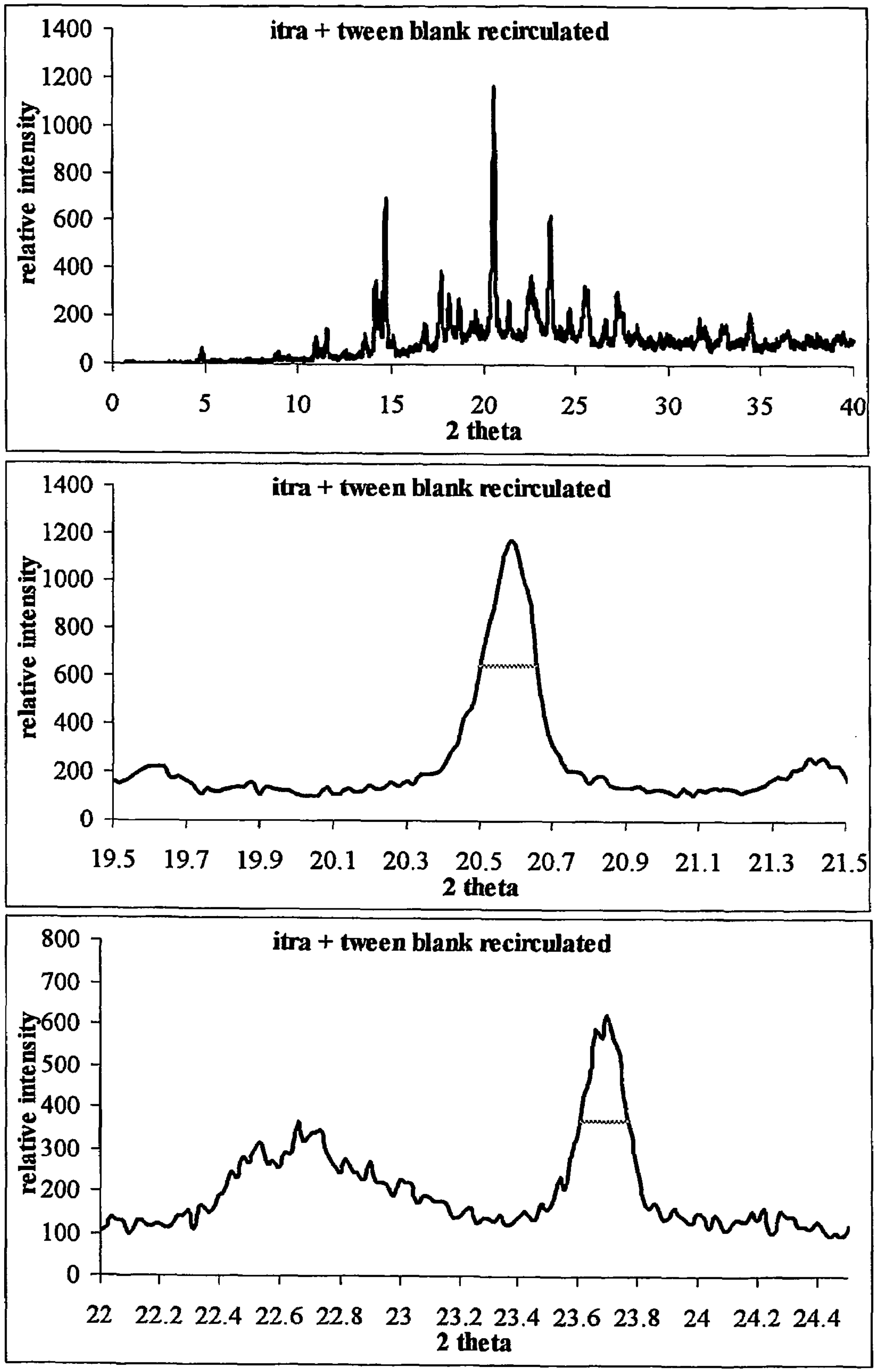
FIG. 6 shows the X-ray diffraction pattern of a mixture of itraconazole and a Tween 80 surfactant.
Figure 7:
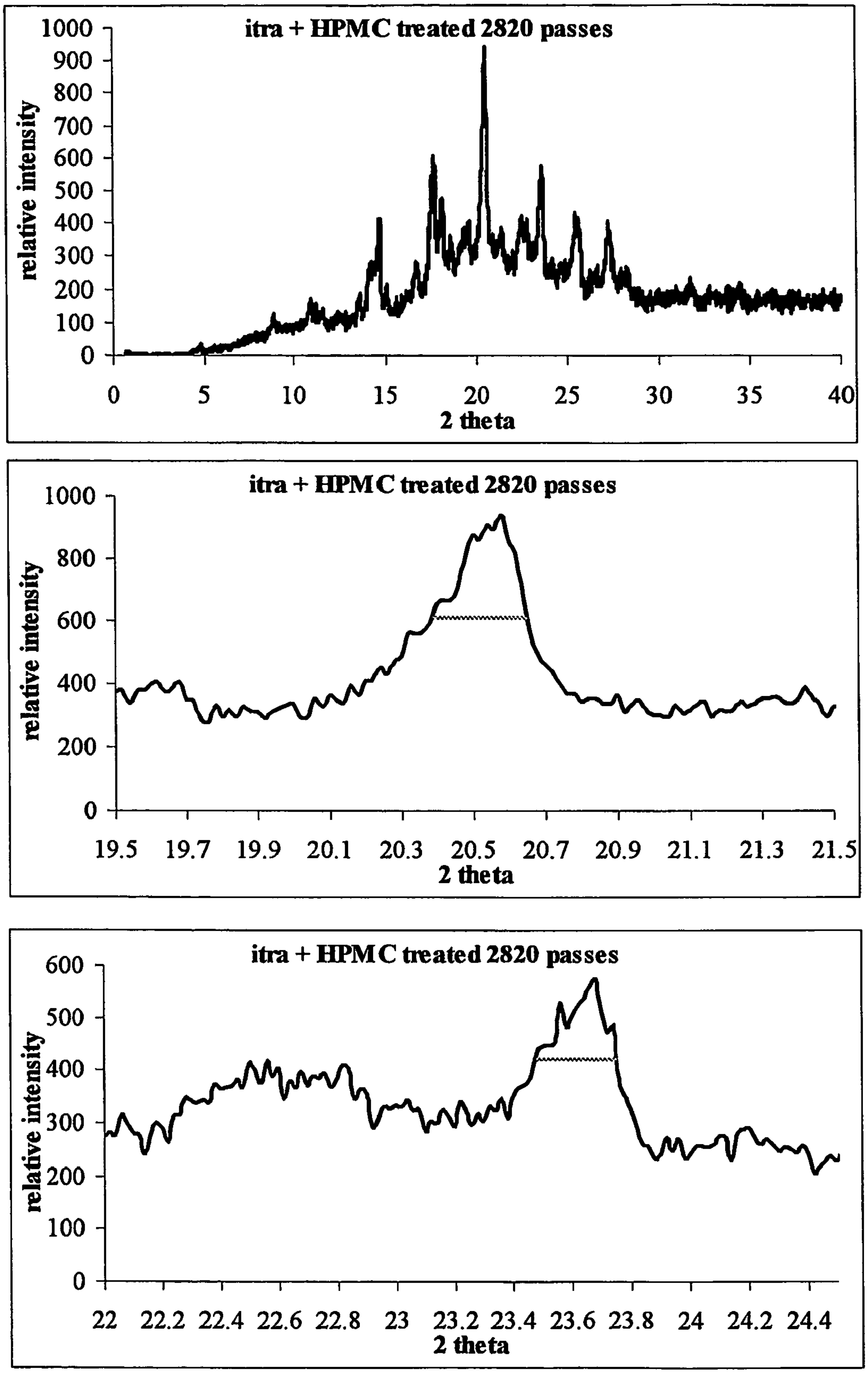
FIG. 7 shows the X-ray diffraction pattern of a magnetically treated mixture of itraconazole, hydroxypropyl methylcellulose (HPMC) and a Tween 80 surfactant.
Figure 8:
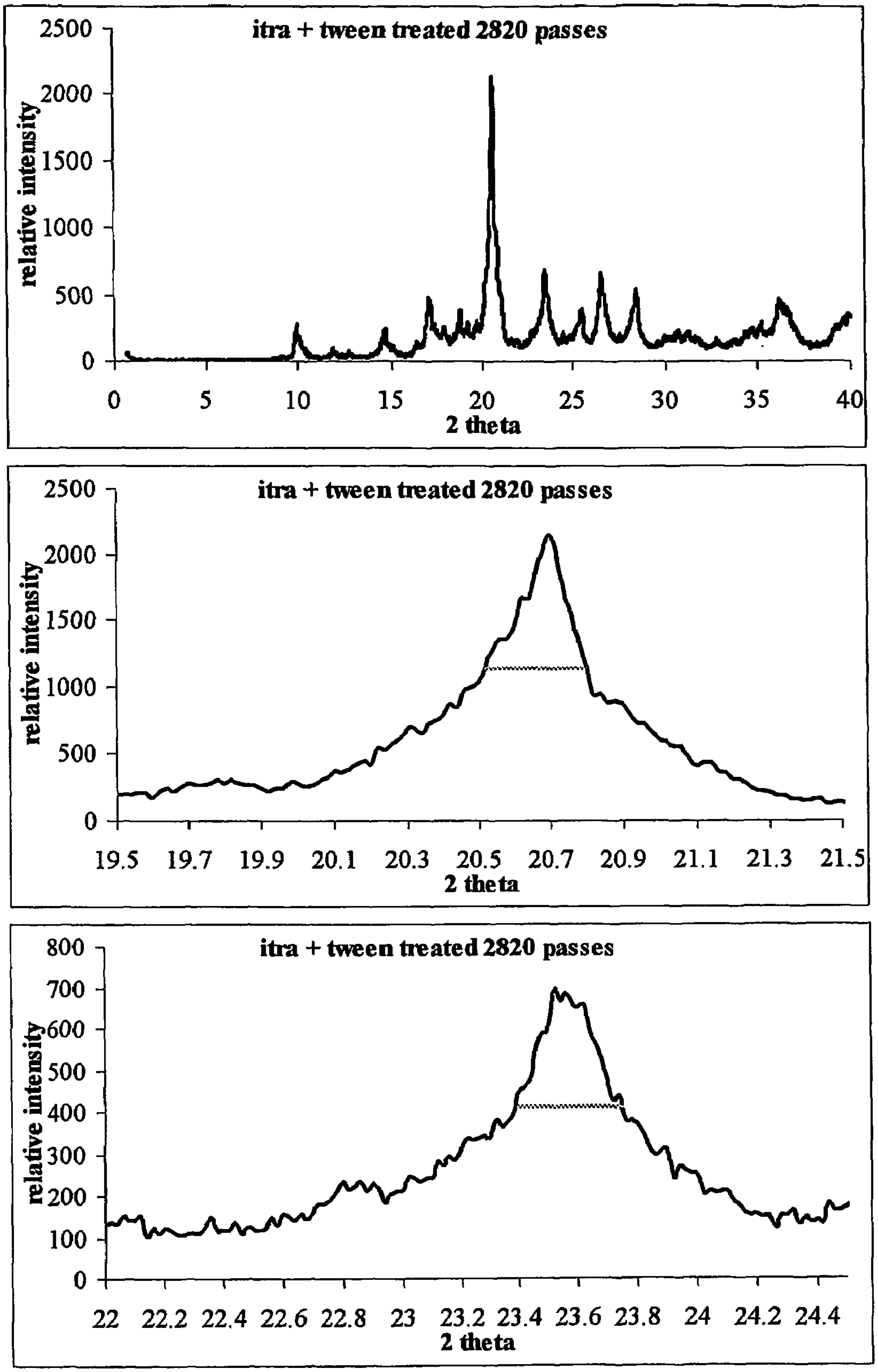
FIG. 8 shows the X-ray diffraction pattern of a magnetically treated mixture of itraconazole and a Tween 80 surfactant.

The X-ray diffractogram from 2θ=0.7 to 2θ=40 of four different samples was measured with a Siemens D5000 matic X-ray diffractometer in steps of 0.02/4 seconds. The first sample was crystalline itraconazole (available from Janssen Pharmaceutica, Beerse, Belgium; abbreviated as "itra" in table 2) (X-ray diffraction pattern shown in FIG. 5). The second sample was prepared by suspending 250 mg of said crystalline itraconazole in 80 ml of bi-distilled water comprising 120 mg of a Tween 80 (same as in example 1) surfactant. This suspension was blank recirculated during 1 hour at 4.7 L/minute in an 80 ml closed system without a magnetic device (FIG. 2B), equaling 3,525 re-circulations. Immediately after blank re-circulation, the dispersion was solidified in a pre-cooled ball that was kept in liquid nitrogen. Water was sublimated in overnight lyophilisation below 1 mbar and a powder sample was obtained (X-ray diffraction pattern shown in FIG. 6). The third sample was prepared by adding 450 mg hydroxypropyl methylcellulose (commercially available under the tradename HPMC 2910, indicating 10% by weight of hydroxypropyl substituent and 29% by weight of methyl substituent on the cellulose, from Sanico, Turnhout, Belgium), 300 mg crystalline itraconazole and 120 mg Tween 80 into 100 ml of bi-distilled water. The resulting suspension was magnetically treated during 1 hour at 4.7 L/minute in a 100 ml closed system with a magnetic device (FIG. 2A), equaling 2,820 recirculations (passes) through the magnetic field at a velocity of 11 m/s. A powder sample was obtained after immediate solidification in liquid nitrogen and lyophilisation (X-ray diffraction pattern shown in FIG. 7). The fourth sample was prepared by adding 250 mg crystalline itraconazole and 100 mg Tween 80 into 100 ml of bi-distilled water. This suspension was magnetically treated during 1 hour at 4.7 L/minute in a 100 ml closed system with a magnetic device (FIG. 2A), equaling 2,820 re-circulations (passes) through the magnetic field at a velocity of 11 m/s. A powder sample was obtained after immediate solidification in liquid nitrogen and lyophilisation (X-ray diffraction pattern shown in FIG. 8).

A comparison of the widths of two diffractogram peaks was made for the four samples (table 2). The occurrence of peak broadening in XRD diffractograms is considered by the skilled person to be a good indication that nano-sized particles are present. The critical size causing peak broadening can also be estimated. Assuming that (1) size of an itraconazole molecule is about 1.5 nm and that (2) the estimated maximal amount of repetitive units causing peak broadening is about 50, then it can be calculated that only particles smaller than 75 nm contribute to peak broadening.

TABLE 2

| sample | 2theta = 20.6 | 2theta = 23.6 |
|---|---|---|
| crystalline itraconazole | 0.19 | 0.22 |
| itra + tween blank recirculated | 0.16 | 0.16 |
| itra + HPMC + tween magnetically treated | 0.27 | 0.27 |
| itra + tween magnetically treated | 0.28 | 0.36 |

The peak widths observed for the magnetically treated samples were clearly higher than in the untreated or blank re-circulated samples, indicating that the magnetically treated samples comprise significantly more nano-sized itraconazole particles.

EXAMPLE 5

Figure 9:
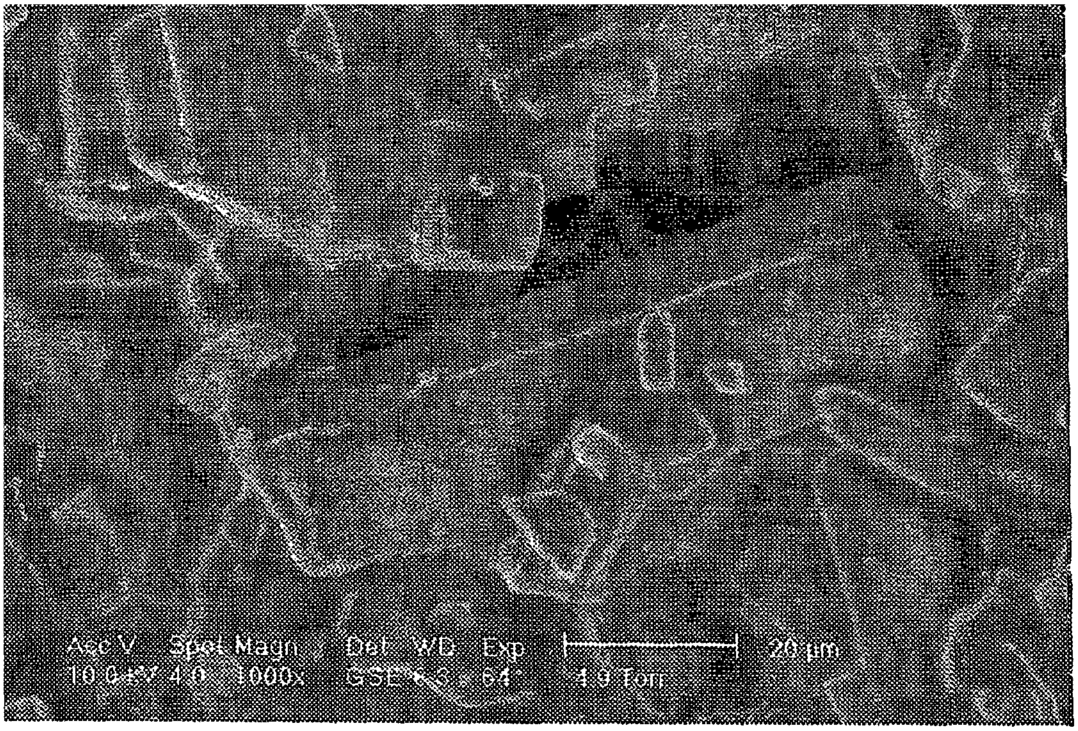
FIG. 9 shows an environmental scanning electron microscopy (SEM) picture of a mixture of itraconazole and a Tween 80 surfactant.

Two samples containing crystalline itraconazole (same as in example 4) were analysed with an environmental scanning electron microscope (ESEM) available from FEI Company (Oregon, United States) under the trade name XL30 ESEM FEG. The first sample was prepared by suspending 250 mg of crystalline itraconazole in 80 ml of bi-distilled water comprising 120 mg of the surfactant Tween 80 (same as in example 1). This suspension was blank re-circulated during 1 hour at 4.7 L/minute in a 80 ml closed system without a magnetic device (FIG. 2B), equaling 3,525 re-circulations. Immediately after blank re-circulation, the dispersion was solidified in a pre-cooled ball that was kept in liquid nitrogen. Water was sublimated in overnight lyophilisation below 1 mbar and a powder sample was obtained (SEM picture shown in FIG. 9). The second sample was prepared by adding 250 mg of crystalline itraconazole and 100 mg of the surfactant Tween 80 in 100 ml of bi-distilled water. This suspension was magnetically treated during 1 hour at 4.7 L/minute in a 100 ml closed system with a magnetic device (FIG. 2A), equaling 2,820 recirculations through the magnetic field at a velocity of 11 m/s. A powder sample was obtained after immediate solidification in liquid nitrogen and lyophilisation (SEM picture shown in FIG. 10).

The ESEM picture of the blank recirculated sample (FIG. 9) shows mainly large particles with an euhedral crystal morphology. In the centre of the picture a large needle-shaped particle with a length of approximately 80 μm and a width of approximately 20 μm is observed. This particle is surrounded by numerous other large particles, with at least one dimension of a few up to several tens of micrometers. Although an important amount of these particles is needle-shaped, having a clearly longer crystal side in one dimension than in the other dimensions, some other large particles have a different shape. But in any case the crystal planes of the large particles are well-shaped. On top of these large particles a small amount of particles with sizes of approximately 1 μm is scattered. These small particles are observed as irregularities on the very smooth crystal planes of the large particles.

Figure 10:
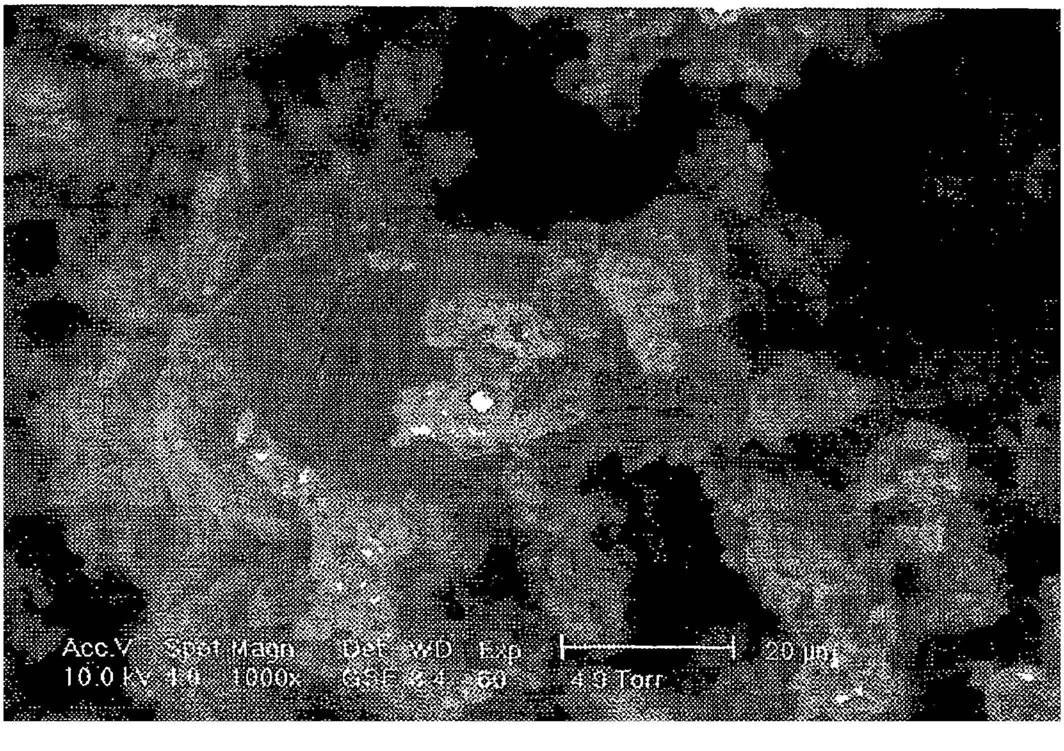
FIG. 10 shows an environmental SEM picture of a magnetically treated mixture of itraconazole and a Tween 80 surfactant.

The centre of the ESEM picture of the magnetically treated sample (FIG. 10) shows a particle with a length of approximately 60 μm and a width of approximately 30 μm. The crystal plane on the top side is smooth in the centre, but irregular near the sides. This crystal plane also shows two large cracks (one with a length of 20 μm, the other with a length of 10 μm). It is clear that the crystal morphology of this large particle is much less well-shaped than the large particles of the blank re-circulated sample. The described particle is the only large particle shown in the FIG. 10. A large amount of randomly shaped aggregates of smaller fragments are scattered around the large particle (FIG. 10). The individual fragments of these aggregates have dimensions of approximately 1 μm.

The clear size and shape differences between the magnetically treated sample (FIG. 10) and the reference sample (FIG. 9) confirm the occurrence of a significant particle size reduction upon magnetic treatment.

EXAMPLE 6

Four different samples containing loperamide (commercially available from Janssen Pharmaceutica, Beerse, Belgium) were prepared and their dissolution profiles were measured. 1 g/l of loperamide and 10 g/l of Aerosil 380 (a silicate commercially available from Degussa, Dusseldorf, Germany) were mixed with bi-distilled water in a mortar. An untreated sample was prepared by fast solidification of part of this suspension in a pre-cooled ball that was kept in liquid nitrogen followed by freeze-drying. Another part of the suspension was pumped through a series of 9 consecutive magnetic devices according to the set-up of FIG. 2C and consisting of (1) a glass funnel (2) tubing (Masterflex Tygon lab I/P 70, Cole-Parmer Instrument Company, Illinois, USA), (3) a pump (Masterflex I/P, Cole-Parmer Instrument Company, Illinois, USA), (4) an internal magnet of the Al—Ni—Co type (commercially available under the tradename W SAN R1/4D from CEPI-CO, Borgerhout, Belgium) and (5) a pre-cooled ball kept in liquid nitrogen. A flow rate of 4.7 l/min was used, equaling a velocity of 11 m/s through the magnetic fields and a residence time in the field of 9 times 136 μs. At the outlet of the system the suspension was immediately solidified in a precooled ball that was kept in liquid nitrogen and followed by lyophilisation. The dissolution profiles of these untreated and magnetically treated samples are given in FIG. 11.

Figure 12:
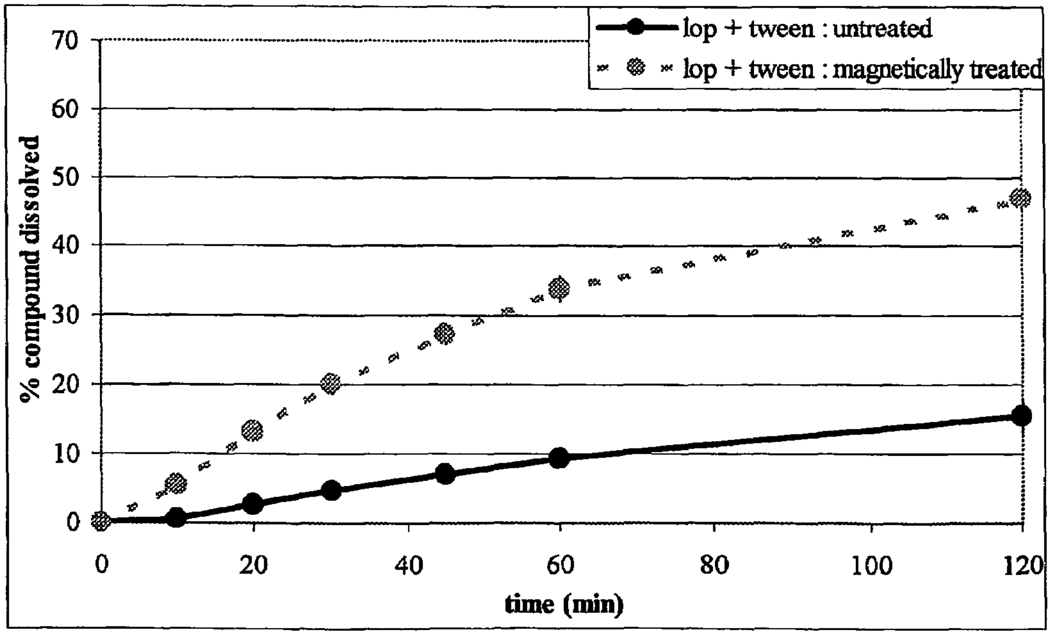
FIG. 12 shows the dissolution profiles of a magnetically treated mixture of loperamide and a Tween surfactant as compared to the untreated mixture.

1 g/l of loperamide and 25 mg/l of the surfactant Tween 80 were mixed with bi-distilled water in a mortar. An untreated sample was prepared by fast solidification of part of this suspension in a pre-cooled ball that was kept in liquid nitrogen followed by freeze-drying. Another part of the suspension was pumped through a series of 9 consecutive magnetic devices according to the set-up of FIG. 2C with the same conditions as described herein. At the outlet of said magnetic system, the suspension was immediately solidified in a pre-cooled ball that was kept in liquid nitrogen and followed by lyophilisation. The dissolution profiles of these untreated and magnetically treated samples are given in FIG. 12.

Dissolution experiments were performed in a SR8 PLUS Hanson dissolution test station (commercially available from Chatsworth, United States) while using the USP 24 method (paddle method, 100 rpm). Samples (corresponding to 16.7 mg of loperamide) were added to 500 ml of dissolution medium being a solution of 0.005 M potassium hydrogen phthalate (commercially available from Acros Organics, Geel, Belgium) and 0.00192 N NaOH in water and the temperature of the dissolution medium was maintained at 37±0.1° C. Samples of 2 ml were taken and immediately replaced with fresh dissolution medium at 10, 20, 30, 45, 60 and 120 minutes respectively and then filtered with PVDF filters of 0.45 μm (commercially available from Acrodisc, Pall Corporation, New York, United States) into HPLC vials (1.5 ml, commercially available from Merck, Darmstadt, Germany). The corresponding concentrations were determined from the calibration curve with HPLC.

The HPLC system used for this determination consisted of LiChroGraph® L-7100 HPLC pump, an auto-sampler model L-7200 equipped with a 100 μl loop, a UV detector model L-7400 set at 220 nm, and an Interface D-7000, all from commercially available from Merck-Hitachi (Darmstadt, Germany). UV signals were monitored and peaks were integrated using the D-7000 HSM software. All chromatographic separations were performed at room temperature. The column used was Hypersil BDS C18 (commercially available from Merck, Darmstadt, Germany). The mobile phase consisted of a 0.001 M acetonitrile/tetrabutylammonium hydrogen sulfate mixture (30:70 by volume) and was degassed by ultrasonication before use. The flow rate amounted to 1 ml/minute. The retention time of loperamide at these conditions was 7 minutes.

Figure 11:
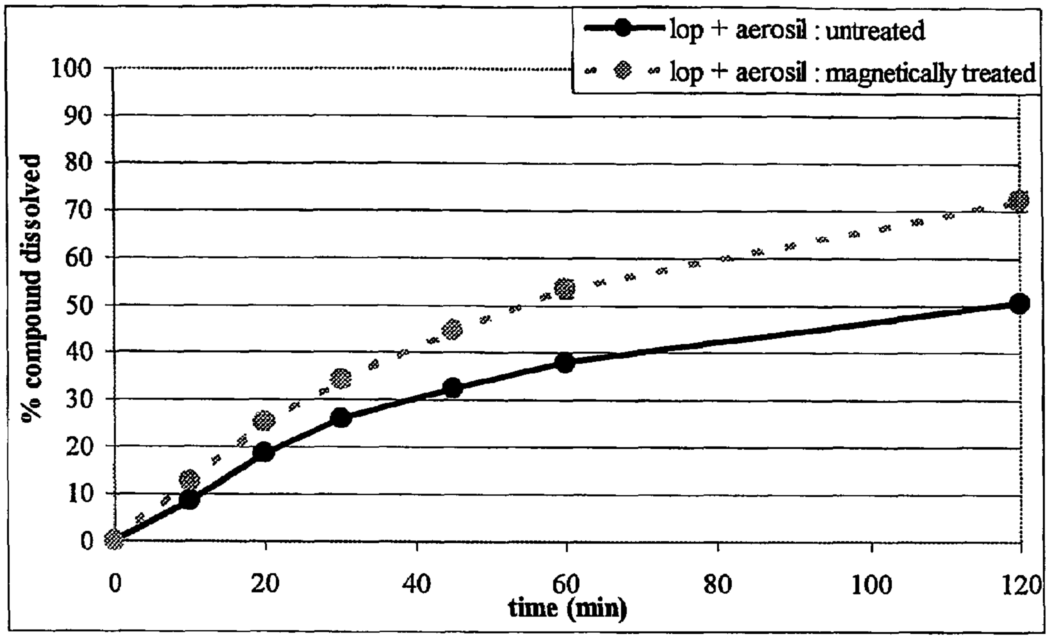
FIG. 11 shows the dissolution profiles of a magnetically treated mixture of loperamide and a silicate as compared to the untreated mixture.

Both in the presence of a silicate (Aerosil) and in the presence of a surfactant (Tween 80), FIGS. 11 and 1 show that the dissolution rate of loperamide is significantly increased by the magnetic treatment of the invention in comparison with the corresponding untreated samples.

The invention claimed is:

1. A method for reducing the average size of biologically active compound solid particles or agglomerates suspended in a liquid by flowing one or more times said liquid having biologically active compound solid particles or agglomerates suspended therein through one or more magnetic fields to reduce the average size of a substantial portion of the biologically active compound solid particles or agglomerates by at least 25%, wherein the linear flow rate of said liquid through each said magnetic field is between 0.25 and 25 m/s.

2. A method according to claim 1, wherein the strength of each said magnetic field is at least about 2,000 gauss.

3. A method according to claim 1, wherein the average size of said biologically active compound solid agglomerates before performing said method is in a range from 10 μm to 100 μm.

4. A method according to claim 1, wherein the average size of a substantial portion of said biologically active compound solid agglomerates after performing said method is reduced to a range from about 0.45 μm to 5 μm.

5. A method according to claim 1, wherein said substantial portion is at least 50% by weight of the suspended solid agglomerates.

6. A method according to claim 1, wherein the average particle size of said biologically active compound solid particles before performing said method is in a range from 0.5 μm to 10 μm.

7. A method according to claim 1, wherein the average particle size of said biologically active compound solid particles after performing said method is reduced to a range from 0.5 nm to 500 nm.

8. A method according to claim 1, wherein said liquid is water or an organic solvent or a combination thereof with water.

9. A method according to claim 1, wherein said biologically active compound solid particles or agglomerates are suspended in said liquid in the form of a slurry and the concentration of said biologically active compound solid particles or agglomerates in said liquid is at least two times the solubility limit of said biologically active compound in said liquid under the physical (temperature, pressure) and chemical (pH) conditions prevailing while flowing said slurry through said magnetic field.

10. A method according to claim 1, wherein said liquid includes one or more stabilizing agents.

11. A method according to claim 1, wherein the residence time of said liquid through each said magnetic field is between 60 microseconds and 10 seconds.

12. A method according to claim 1, wherein the biologically active compound is in a crystalline form or an amorphous form.

13. A method according to claim 1, wherein the biologically active compound is a drug classifiable as Class II or Class IV of the Biopharmaceutical Classification System.

14. A method according to claim 1, wherein the biologically active compound is a drug having a water-solubility below 2 mg/ml.

15. A method according to claim 1, wherein the biologically active compound is a cosmetic agent, a diagnostic agent, a herbicide, an insecticide, a biocide or a fungicide.

16. A process for manufacturing a biologically active compound formulation, said biologically active compound being in the form of solid particles or agglomerates, said process comprising a step of reducing by at least 25% the average size of a substantial portion of said biologically active compound solid particles or agglomerates by suspending them in a liquid and by flowing one or more times said liquid having biologically active compound solid particles or agglomerates suspended therein through one or more magnetic fields.

17. A process according to claim 16, wherein said process further comprises one or more post-processing steps performed following the size reducing step.

18. A process according to claim 16, wherein said post-processing step is a drying step for substantially removing the liquid in which the biologically active compound solid particles or agglomerates are suspended during the size reducing step.

19. A process according to claim 16, wherein said post-processing step comprises mixing an adjuvant together with the optionally dried particles or agglomerates with reduced size.

20. A process according to claim 16, wherein said biologically active compound is a drug having a water-solubility below 2 mg/ml.

21. A process according to claim 16, wherein said biologically active compound is a cosmetic agent, a diagnostic agent, a herbicide, an insecticide, a biocide or a fungicide.

* * * * *

UNITED STATES PATENT AND TRADEMARK OFFICE

CERTIFICATE OF CORRECTION

PATENT NO. : 7,666,307 B2
APPLICATION NO. : 10/595119
DATED : February 23, 2010
INVENTOR(S) : Van Den Mooter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 688 days.

Signed and Sealed this

Seventh Day of December, 2010

David J. Kappos

*Director of the United States Patent and Trademark Office*